(12) United States Patent
Morin et al.

(10) Patent No.: US 7,376,519 B2
(45) Date of Patent: May 20, 2008

(54) METHOD FOR REDUCING THE COMPUTATION RESOURCES REQUIRED FOR DETERMINING DAMAGE IN STRUCTURAL HEALTH MANAGEMENT SYSTEM

(75) Inventors: Brent A. Morin, Cave Creek, AZ (US); Grant A. Gordon, Peoria, AZ (US); Joseph J. Nutaro, Phoenix, AZ (US); Steven R. Thompson, Phoenix, AZ (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/976,712

(22) Filed: Oct. 29, 2004

(65) Prior Publication Data
US 2006/0106551 A1    May 18, 2006

(51) Int. Cl.
*G01B 5/28* (2006.01)
*G01B 5/30* (2006.01)

(52) U.S. Cl. .............. 702/35; 73/587; 73/594; 73/632; 702/33; 702/34; 702/36; 702/38

(58) Field of Classification Search .............. 702/35, 702/34, 36, 38; 73/589, 594, 632
See application file for complete search history.

(56) References Cited

U.S. PATENT DOCUMENTS

| | | | |
|---|---|---|---|
| 4,419,900 A | 12/1983 | Scott et al. | |
| 5,184,516 A | 2/1993 | Blazic et al. | |
| 5,383,133 A | 1/1995 | Staple | |
| 5,774,376 A | 6/1998 | Manning | |
| 6,006,163 A | 12/1999 | Lichtenwalner et al. | |
| 6,076,405 A | 6/2000 | Schoess | |
| 6,192,759 B1 | 2/2001 | Schoess | |
| 6,370,964 B1 | 4/2002 | Chang et al. | |
| 6,396,262 B2 | 5/2002 | Light et al. | |
| 7,117,742 B2* | 10/2006 | Kim .......................... | 73/587 |
| 2001/0022514 A1 | 9/2001 | Light et al. | |
| 2001/0047691 A1 | 12/2001 | Dzenis | |
| 2002/0154029 A1 | 10/2002 | Watters et al. | |
| 2003/0009300 A1 | 1/2003 | Giurgiutiu | |
| 2003/0167141 A1 | 9/2003 | Staszewski | |
| 2003/0233876 A1 | 12/2003 | Huang et al. | |
| 2005/0228597 A1* | 10/2005 | Giurgiutiu et al. ............ | 702/35 |

FOREIGN PATENT DOCUMENTS

| | | |
|---|---|---|
| EP | 0 067 531 A2 | 12/1982 |
| WO | WO 00/64737 | 11/2000 |
| WO | WO 02/062206 A2 | 8/2002 |
| WO | WO 03/106958 A2 | 12/2003 |

* cited by examiner

*Primary Examiner*—John Barlow
*Assistant Examiner*—Sujoy Kundu

(57) ABSTRACT

A method for determining damage in a structural health monitoring system comprising a plurality of sensors distributed across a structure is disclosed. The method includes decomposing the plurality of sensors into a plurality of sub-arrays. Each sub-array is associated with a current sensor. For each sub-array, data is collected, the data corresponding to electrical signals produced by waves initiated by the current sensor and detected by a receiving sensor. The data is used to calculate a damage measurement for the sub-array. Then, the damage measurement determined for each sub-array is combined to determining an overall damage assessment from the combined damage measurements.

21 Claims, 6 Drawing Sheets

METHOD FOR REDUCING THE COMPUTATION RESOURCES REQUIRED FOR DETERMINING DAMAGE IN STRUCTURAL HEALTH MANAGEMENT SYSTEM

TECHNICAL FIELD

This invention relates to the field of structural health management, and more specifically to a method for reducing the computation resources required for determining damage in a structural health management system

BACKGROUND

Nondestructive testing is a procedure for determining the quality or characteristics of a structure without permanently altering the structure or the structure's properties. Examples include ultrasonic and radiographic inspection. In the avionics field, nondestructive evaluations of airplane components are done to insure the structural integrity of the airplane. In typical airplane maintenance approaches, a certified inspector performs one or more nondestructive tests on the aircraft. This process may be repeated at regular intervals to monitor the structural health of the aircraft.

While this type of nondestructive testing scheme can be effective, it has several drawbacks. First, the test typically needs to be conducted by trained inspectors, which can incur significant costs, including the potential loss of operational revenue, when having an inspector perform the tests on site. Second, to enable efficient analysis and repetitive comparison over time, a non-subjective decision process driven by inspection data, inspection method parameters, location, decision criteria, and material properties within the context of the structure being inspected may be required. Current inspection approaches may not preserve these necessary components. Although each inspection can be analyzed individually, a collection of inspections may not be analyzed in toto.

To resolve some of the drawbacks of current nondestructive schemes, other structural health management schemes have been developed. In one structural health management technique, ultrasonic transducers can be placed, for example, on the fuselage of the aircraft to be tested. The ultrasonic transducers are then coupled to an onboard testing computer. The testing computer can be used to run nondestructive tests when needed by using the installed ultrasonic transducers.

The above-described system allows for nondestructive testing to be done without having an inspector bring equipment to the aircraft. Additionally, the automated inspection and determination of the state of the inspected material preserves accurate location data, as well as the associated data used to perform the inspection and make the determination. This allows multiple self-referential inspections of an area over an extended period of time, enabling correlation, trending and other sophisticated analysis of the inspection data across vehicles and over time.

Damage assessments can be made by running various damage algorithms using data collected by the sensors. In large structural health monitoring systems, the amount of data to process is very large, requiring processors with high bandwidth capabilities and large amounts of memory, if large blocks of data are processed concurrently. This adds additional costs and complexities to the system, which is undesirable.

BRIEF SUMMARY

In one embodiment of the present invention, a method for determining damage in a structural health monitoring system comprising a plurality of sensors distributed across a structure is disclosed. The method includes decomposing the plurality of sensors into a plurality of sub-arrays. Each sub-array is associated with a current sensor. For each sub-array, data is collected, the data corresponding to electrical signals generated by the electro-mechanical transduction of elastic waves initiated by the current sensor and detected by a receiving sensor. The data is used to calculate a damage measurement for the sub-array. Then, the damage measurement determined for each sub-array is combined to determining an overall damage assessment from the combined damage measurements.

In one embodiment of the method, the damage measurement is calculated by first comparing the damage measurement to a predetermined baseline measurement. Then a changed damage measurement is determined from the difference between the damage measurement and the predetermined baseline measurement. The changed damage measurement determined for each sub-array is combined to determine an overall damage assessment.

In another embodiment of the present invention a structural health monitoring system is disclosed. The system includes a plurality of sensors mounted on a structure. The plurality of sensors are decomposed into a plurality of sensor sub-arrays with each sensor in each sub-array configured to receive signals indicative of the internal composition of the structure and generated by a current sensor in the sub-array. The system further includes a processor coupled to the plurality of sensors. The processor is configured to calculate a sub-array damage assessment for each sub-array based on the signals received by the sensors. The processor is further configured to calculate an overall damage assessment from each of the sub-array damage assessments.

In another embodiment of the present invention the processor is further configured to generate a sub-array change measurement by comparing the sub-array damage assessment to a baseline damage assessment. The processor can combine the sub-array change measurements to form the overall damage assessment.

In yet another embodiment of the present invention the system further comprises a memory coupled to the processor. The memory stores a table comprising the plurality of sensors listed by a collection of overlapping sub-arrays.

BRIEF DESCRIPTION OF THE DRAWINGS

The present invention will hereinafter be described in conjunction with the following drawing figures, wherein like numerals denote like elements, and.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description. While the invention is discussed in an avionics embodiment, the teachings of the present invention are applicable to many different fields of endeavor.

Figure 1:
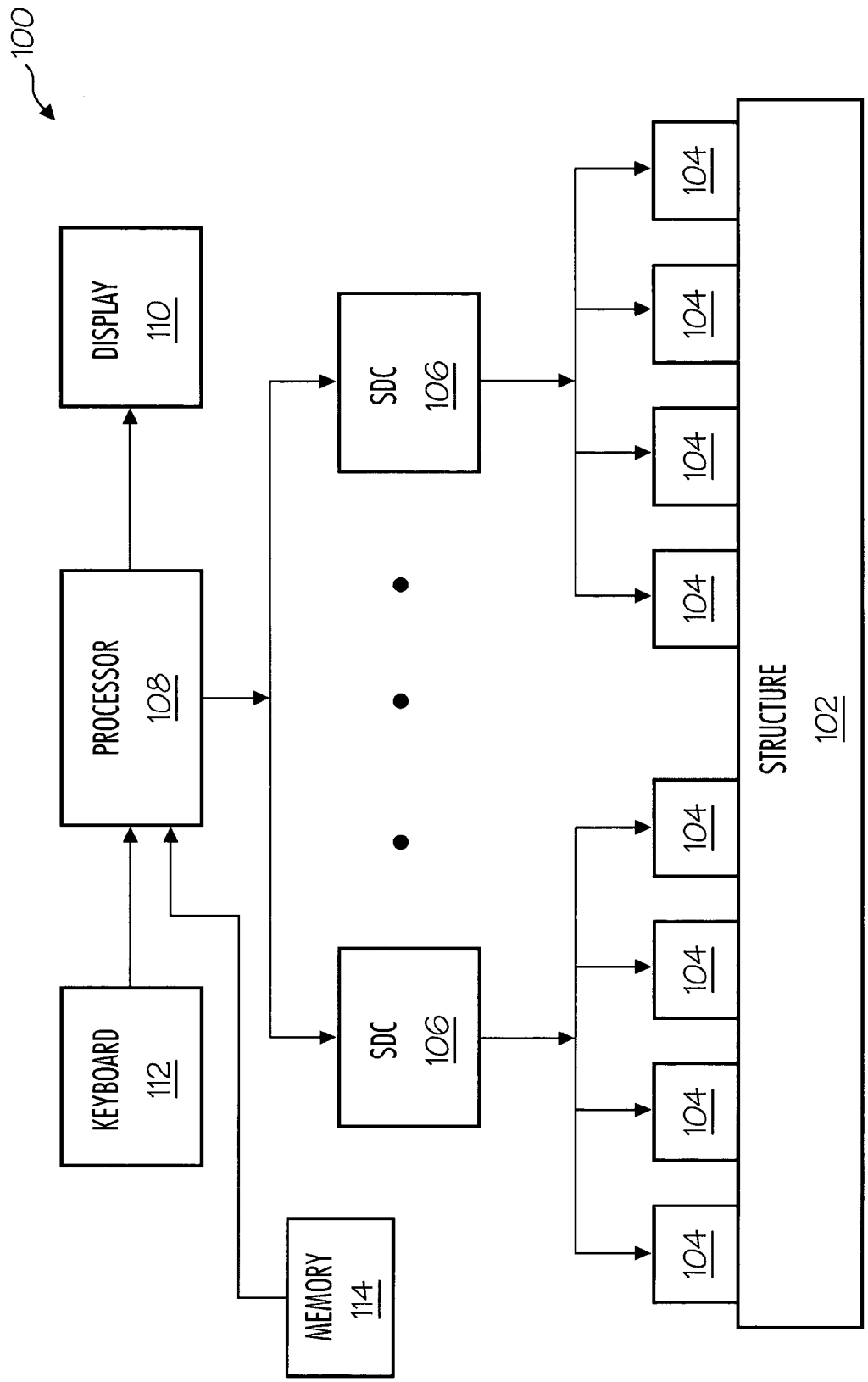
FIG. 1 illustrates an exemplary structural health mounting system in accordance with the teachings of the present invention.

FIG. 1 illustrates an exemplary structural health management system 100 in accordance with the teachings of the present invention. Structural health management system 100 includes a plurality of sensors 104 coupled to one or more sensor data collectors 106. Each sensor 104 is mounted to a structure 102 to be tested. The output of all the sensor data collectors 106 are provided as an input to at least one structural health monitoring processor 108. Various inputs and outputs can be provided to structural health monitoring processor 108. For example, processor 108 can be coupled to various input/output devices including a display 110, a keyboard 112 and the like. Processor 108 also has a memory 114 associated with it.

Sensors 104 can be ultrasonic transducers that convert electrical signals into mechanical vibrations and mechanical vibrations into electrical signals. Typically, sensor 104 converts electricity into mechanical vibrations that propagate waves in the structure 102 to which the sensor 104 is coupled through elastic deformation (known as elastic waves). The propagated waves interact with various features within the structure 102 such as flaws or defects. The sensor 104 can receive transmitted and reflected waves and convert the mechanical vibrations caused by these waves into electrical signals. These electrical signals can then be analyzed to determine if there are any flaws or defects in the structure 102.

The amount of time it takes for a wave to travel between two sensed locations is known as the time-of-flight. In addition to the time-of-flight, signal amplitude, signal energy (area under the rectified voltage curve) and other features of an elastic wave received by a sensor 104 can be used in models to predict the underlying damage state of the area traversed by the propagated elastic wave. Various features within the structure 102, such as fatigue cracks or other structural flaws, can be identified and located based on these values obtained from data collected by sensor 104 and others.

While many different designs for sensors 104 exist, in one embodiment, sensor 104 is a piezoelectric transducer. Piezoelectric transducers produce mechanical vibrations when an electric signal is applied and produce electrical signals when receiving mechanical vibrations. Typically, piezoelectric transducers use piezoelectric ceramics that can be engineered to produce different wave modes.

Different types of waves induced by piezoelectric transducers can be used in nondestructive testing. In an embodiment of the present invention, the sensors 104 produce Lamb waves in structure 102. Lamb waves propagate throughout the entire thickness of plate-like structures, such as the composite material used for the skin of an aircraft. Lamb waves are a form of guided elastic waves distinct from the bulk waves used in traditional ultrasonic inspections. Lamb waves traverse along the plate-like structures while exciting material throughout the plate's thickness. As a consequence, the use of Lamb waves allows for distributed sensor schemes to examine the composite plate-like structure over a given area without the need to scan the transducers over certain areas.

Sensor data collectors (SDCs) 106, in one embodiment of the present invention, collect data from the sensors 104 in the form of electrical signals and send the data to processor 108 for evaluation. In another embodiment, sensor data collectors 106 collect data and can perform some analysis on the data prior to sending the data to the processor 108. By providing multiple sensor data collectors 106, if one sensor data collector 106 was to fail, the entire structural health management system 100 would not fail. Additionally, in one embodiment, SDCs 106 accept multiple sensor inputs and provide a single high speed data output; resulting in a reduction in the amount of wiring required between the sensors 104 and the processor 108. While SDCs are useful in reducing wiring and complexity, in one embodiment of the present invention, SDCs 106 are not used and data is routed from the sensors 104 to the processor 108.

Processor 108 can receive data from the sensors 104, either directly or via SDCs 106. Processor 108 can also process the data to evaluate the structural health of the structure 102. Processor 108 can also receive data from sensors 104 and perform damage assessment analysis. Processor 108 can be a commercial off the shelf processor and any components necessary to allow processor 108 to process data. Processor 108 can couple to input/output devices such as the display 110, such as a CRT or LCD display, that displays information to a user.

Memory 114 can provide storage needed for programs executing on the processor 108 such as data and computer code needed by the processor to determine damage in the system 100. Memory 114 can be any of the various types of memory appropriate for system 100, including random access memory (RAM) magnetic storage, optical storage and the like. While memory 114 is shown as a single unit in FIG. 1, memory 114 can be a combination of memories, each providing a different function, such as a first memory for short term use to support processor execution and a second memory for long term storage.

Structure 102 can be any one of numerous types of material of interest to be tested. In one embodiment, structure 102 is a composite material used for the skin of an aircraft. In one exemplary embodiment, structure 102 is a plate-like composite material such as the material used in to form modem aircraft skin.

Figure 2:
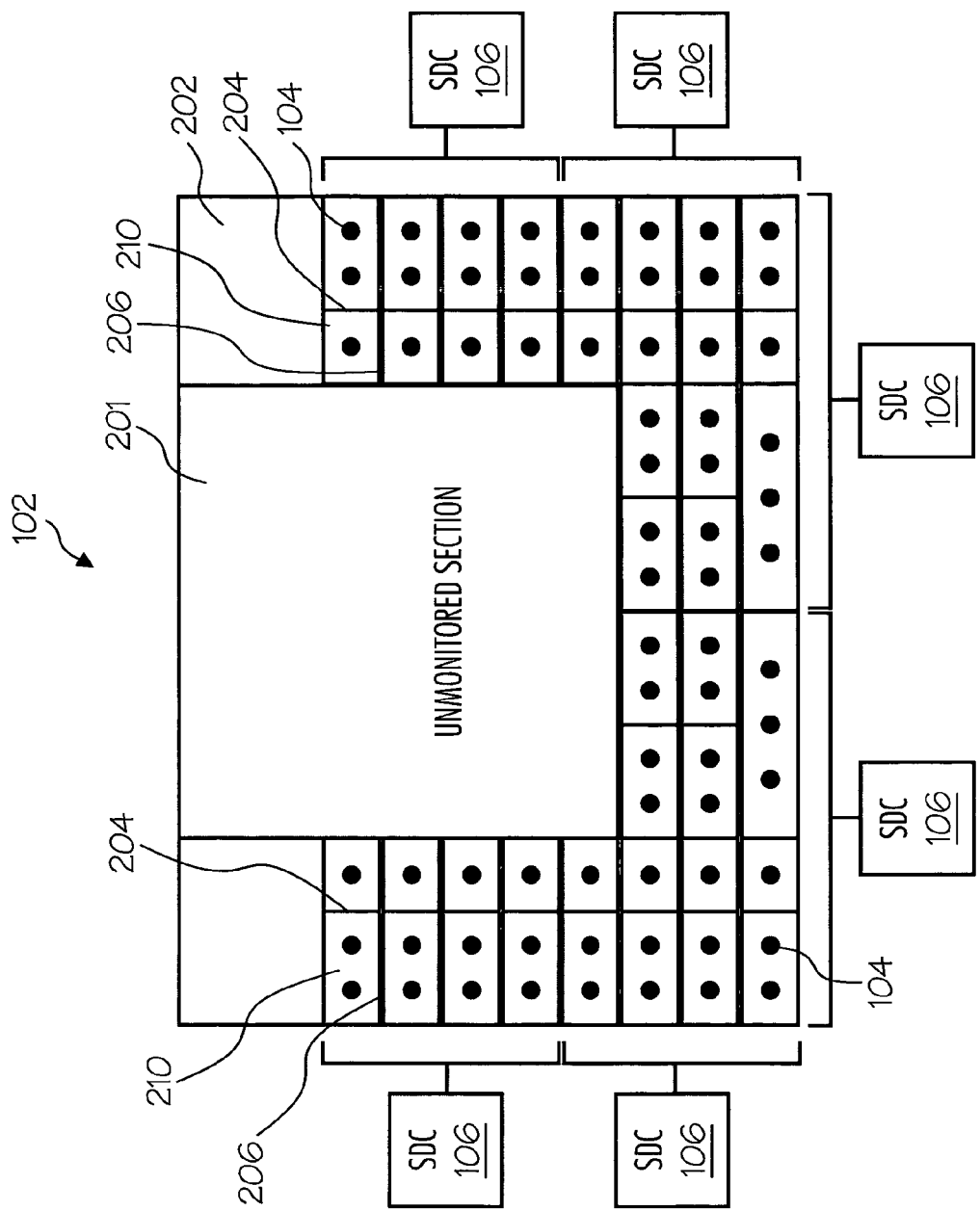
FIG. 2 illustrates the placement of sensors around a non-monitored section of an aircraft in accordance with the teachings of the present invention.

An exemplary arrangement of the sensors 104 and SDCs 106 in a structural health management system 100 is illustrated in FIG. 2. To avoid unnecessarily complicating FIG. 2, SDCs 106 are illustrated as associated with a grouping of sensors in FIG. 2. As better viewed in FIG. 1, each sensor 104 will be coupled to one of the SDCs 106. FIG. 2 illustrates an exemplary section of structure 102 to be tested. As shown in FIG. 2, one or more sensors 104 are placed on the inside surface 202 of the structure 102 in sections 210 bordered by a pair of stringer members 206 and a pair of frame members 204. In the embodiment of FIG. 2, the structure 102 is adjacent to a non-monitored area 201. Non-monitored area 201 can be any area not monitored by the system 100 and, in an avionics embodiment where the structure 102 is aircraft skin, the non-monitored area 201 can be a structure such as a window, door and the like. As noted, FIG. 2 illustrates the inside surface 202 of the structure 102; the outside of the structure 102 is not visible in this perspective.

In operation, each sensor 104 can produce, transmit and receive elastic wave energy. The elastic wave energy, produced by a sensor 104 converting mechanical energy to an elastic wave, can manifest itself in a variety of forms such as transient Lamb Waves, bulk waves, Rayleigh waves and the like. These elastic waves can be transmitted, reflected, refracted, mode converted and attenuated as the elastic waves propagate through out the structure, interacting with internal features. As discussed previously, characteristics of any defect can be determined, in part, from the time-of-flight, signal amplitude, and signal energy (area under the rectified voltage curve) of the propagated elastic waves as received by a sensor. Additionally, the time of flight between sensors or between the start of an elastic wave and its return from reflection of a boundary can be used to determine distances between sensors and between sensors and boundaries.

In one embodiment, to conduct a damage assessment, sensors are pulsed sequentially and data is collected at surrounding sensors. Once each sensor has been pulsed and all data collected, a damage assessment algorithm can be used to evaluate the data. In a large complex system with many sensors, the amount of data required to be processed can be considerable. The extensive amount of data to be analyzed requires large amounts of memory and high bandwidth processors. In one embodiment of the present invention, to alleviate at least part of the complexities of damage calculations, the entire array of sensors 104 in the system 100 is decomposed into a plurality of smaller sub-arrays and damage calculations are then performed on the subsets. In at least one embodiment, the sub-arrays overlap. The results are combined to determine an overall damage assessment.

Figure 3:
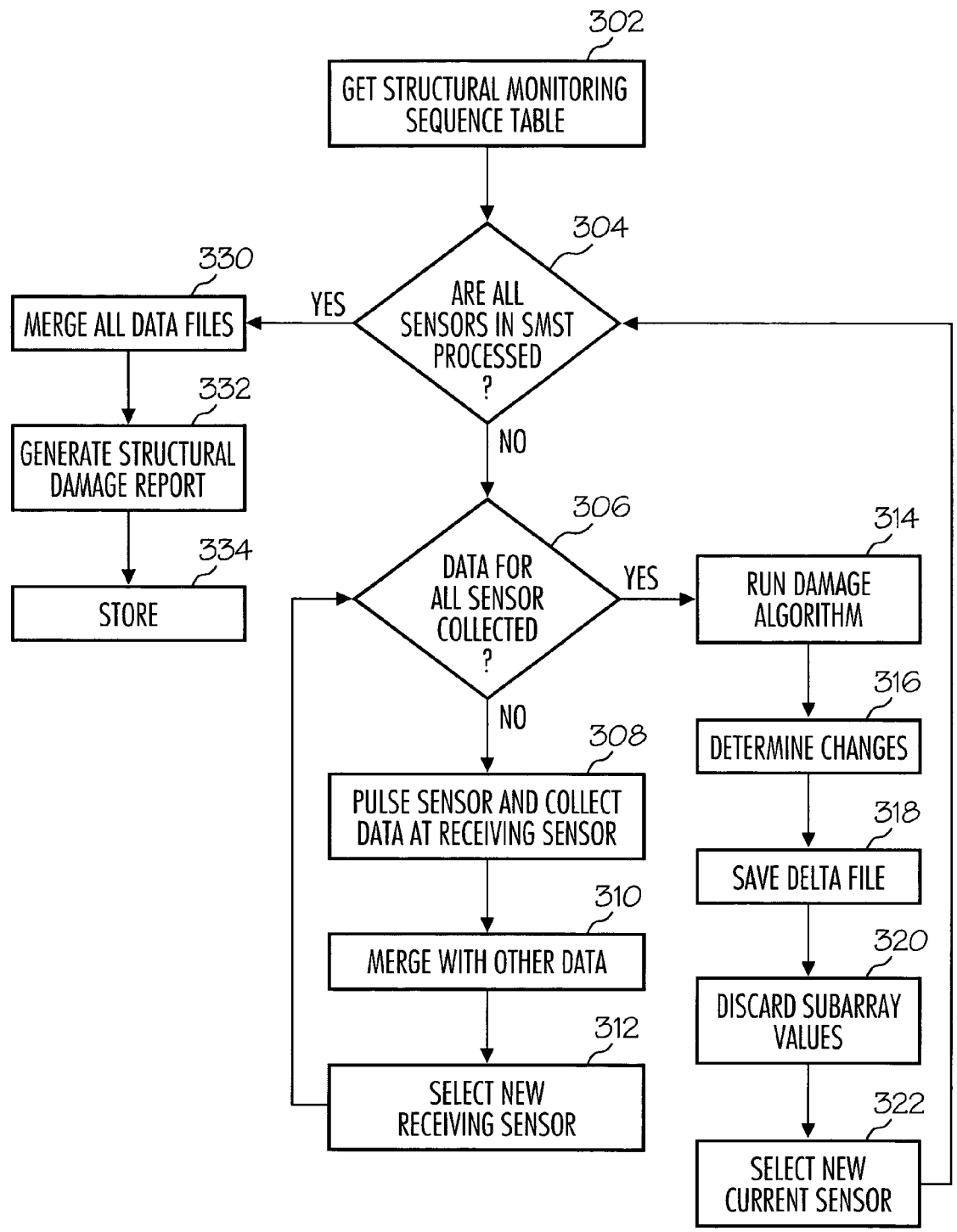
FIG. 3 is a flowchart of a method for determining damage in a structural health management system in accordance with the teachings of the present invention.
Figure 4:
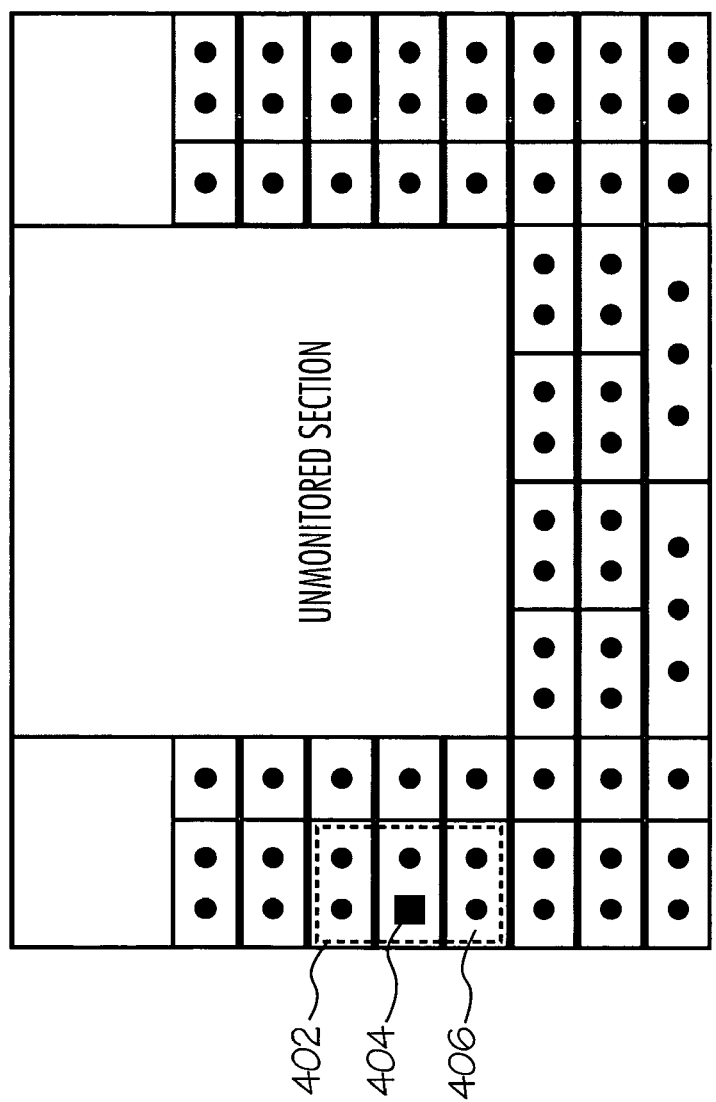
FIGS. 4-6 illustrate overlapping sub-arrays of sensors for use in a method for determining damage in a structural health management system in accordance with the teachings of the present invention.
Figure 5:
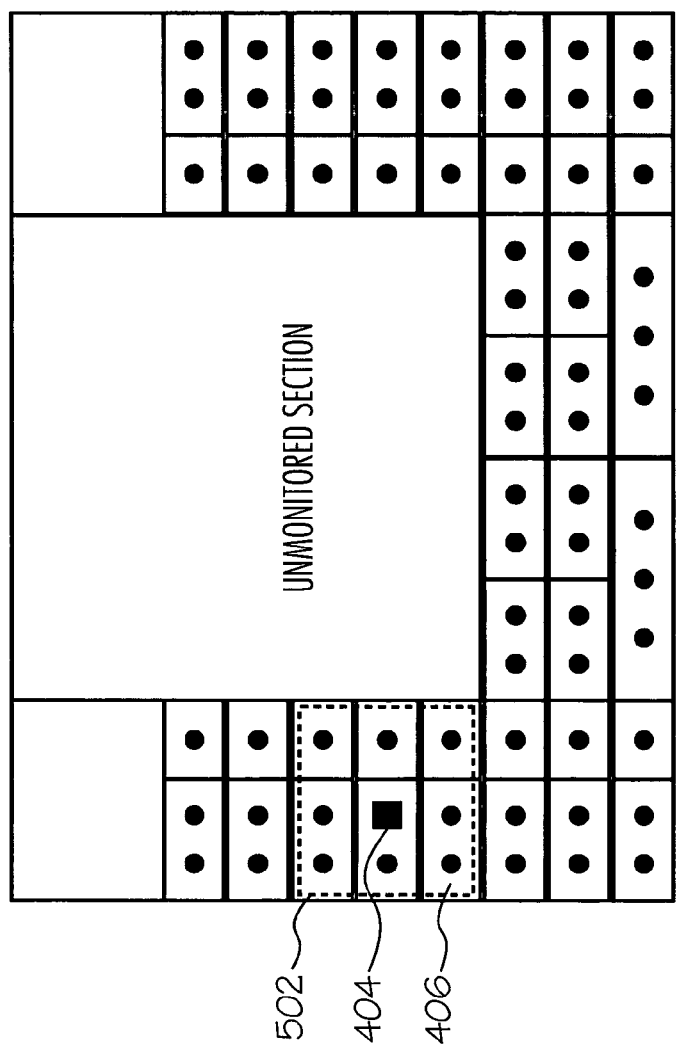
Figure 6:
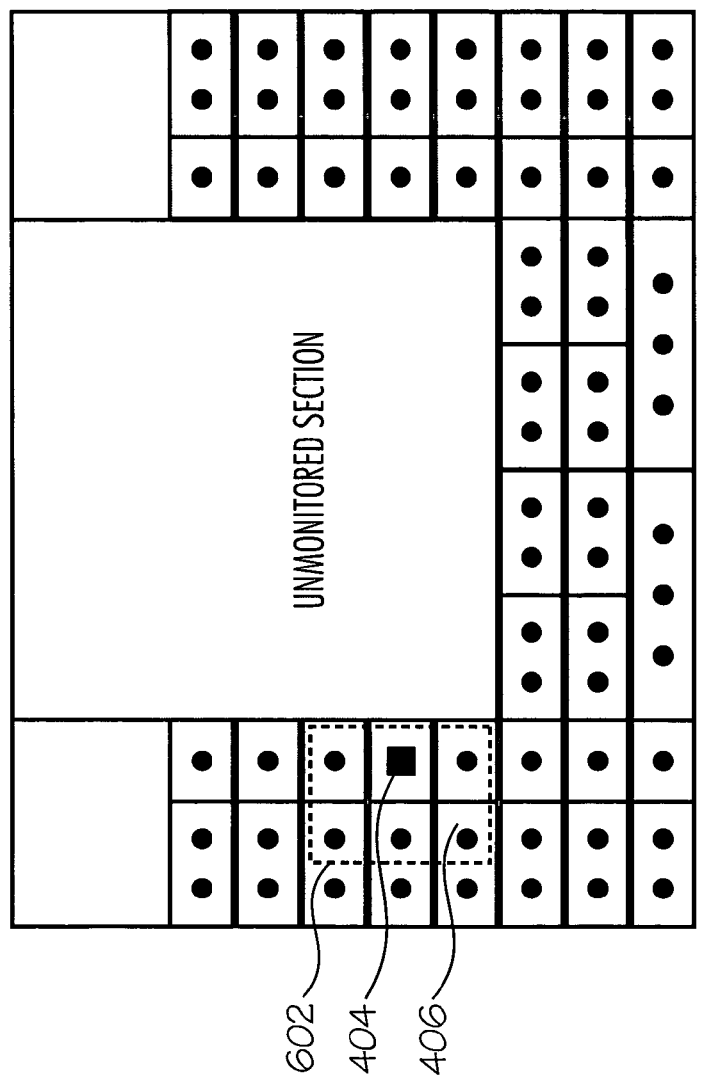

FIGS. 3-6 illustrate a method for providing overall damage assessment using a series of overlapping localized damage assessment areas. With reference to FIGS. 4-6, the method of the present invention divides all of the sensors 104 in the system 100 into a plurality of, typically, an overlapped sub-array such as sub-arrays 402, 502 and 602. Each sub-array 402-602 is based around a current sensor 404 and one or more neighbor sensors 406. The neighbor sensors 406, in one embodiment, are adjacent to the current sensor 404. While FIGS. 4-6 illustrate the neighbor sensors 406 as immediately adjacent to current sensor 404, sensors 406 further from the current sensor 404 can also be considered a neighbor sensor in other embodiments of the present invention. Note that in FIG. 4-6, there is an overlap of sensors 104 in sub-arrays 402, 502 and 602.

An exemplary method for calculating damage in a structure health management system 100 is illustrated in FIG. 3. In a first step 302, a structural monitoring sequence table (SMST) is formed. The SMST, in one embodiment, provides a listing of all of the sensors 104 in the system 100 divided into a plurality of sub-arrays 402. In the present invention, for each sub-array 402 the current sensor 404 initiates the elastic wave in the material (the current sensor, which can also be referred to as the pinging sensor). The neighbor sensors 406 receive the signal initiated by the current sensor 404 as influenced by any flaw or defects in the material. Since the current sensor 404 is also capable of receiving the propagating wave, the receiving sensors in any sub-array 402 is the combination of the neighbor sensor 406 and the current sensor 404. Thus, in one embodiment, entries in the SMST can be expressed as:

$A_{ij}$=(current sensor$_i$, receiving sensor$_j$)

In one embodiment, the SMST can be generated once for a system and stored. Then the SMST can be retrieved when needed. Indeed, for many similar systems, the SMST can be generated based on design documents, system schematics or other reference.

Next, in step 304, it is determined if all sensor entries in the SMST have been processed. In a preferred embodiment there are entries associated with each sensor 104 in the system. Each sensor 104 in the SMST is processed once each sub-array 402 has been processed or, equivalently, once each sensor 104 in the system 100 has been the current sensor. If all SMST sensor entries have not been processed, in step 306, it is determined if data from all sensors 104 in the current sub-array 402 has been collected. As discussed previously, the sensor sub-array data is comprised of data from each receiving sensor, which is the same as each sensor 104 in the sub-array 402.

Next, damage calculations can be done on each sub-array, one-sub-array at a time. If all the data from each sensor 104 in the sub-array 402 has not been processed, in step 308, the current sensor 404 for the sub-array 402 is pulsed and the resultant wave is detected at one of the receiving sensors (the active receiving sensor). The data is collected from the active receiving sensor and is merged with any other data already gathered for sensors 104 in the current sub-array 402 in step 310. In step 312, a next receiving sensor is selected as the new active receiving sensor. If there are still sensors in the current sub-array 402 that have not been used as the active receiving sensor, as determined in step 306, steps 308-312 are repeated using the current sensor and the new active receiving sensor.

Once data is collected for all receiving sensors for the current sensor (that is, once box 306 evaluates to yes, which occurs once all of the data in a given sub-array has been collected), a damage algorithm is run on the data from the sub-array, in step 314. Various different damage algorithms have been derived for use in evaluating data generated by ultrasonic testing. The damage algorithm used to evaluate the sub-array data can, therefore, be varied within the scope of the present invention. After the damage algorithm is calculated for the current sub-array 402, in step 316, the results can be compared to a baseline result, obtained prior to the current test and stored in a database. A delta or change file can be generated, the delta file comprising the difference between the current test data and the baseline values. The delta file values are saved, in step 318, for further use in step 330.

In step 320, to save storage space, the sub-array 402 data from the current sub-array 402 can be discarded. In step 322, the next current sensor 404 is chosen. This corresponds to the next sensor sub-array 402. After the next current sensor 404 is chosen, it is determined in step 304 if all sensors entries have been processed. That is equivalent to determining if all of the sub-arrays 402 have been processed. If not, then data is collected for the next current sensor 404 and its receiving sensors in steps 306-312 and the damage algorithm is calculated for the next current sensor and its receiving sensors in steps 314-322.

If all sensors in the system (equivalent to all sub-arrays 402) have been evaluated, then in step 330 the collected delta files are merged and overall damage is determine using an appropriate damage algorithm. This will result in the overall damage calculation for the entire set of sensors 104. Next, in step 332, the overall damage results are processed and a structural damage report is created. The structural damage report can be saved to mass storage in step 334 for future reference.

While the method as shown in FIG. 3 illustrates the use of a SMST, that is for exemplary purposes only. Indeed, sensors 104 can be grouped into sub-arrays without the use of a table. Additionally, while the method described above discussed the use of a change file to determine the damage in a system, damage can also be determined without the use of a delta file computed on a sub-array basis.

By decomposing a large system of data collectors into a series of overlapping sub-arrays, smaller amounts of processor throughput and memory are required, resulting in cost and weight savings. Also, the various connections between the sensors and processors would require less bandwidth. In one embodiment, calculations are done at the processor 108. However, in an alternative embodiment, the SDCs 106 perform at least some of the calculations needed to execute the method in accordance with the teachings of the present invention.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. A method for determining damage in a structural health monitoring system comprising a plurality of sensors distributed across a structure, the method comprising:
dividing the plurality of sensors into a plurality of overlapping sub-arrays comprising a set of sensors, each overlapping sub-array comprising one or more sensors from the set of sensors that are part of the set of sensors for another sub-array, each sub-array comprising a current sensor;
for each sub-array:
collecting data from each sensor in the sub-array, the data corresponding to electrical signals produced by waves initiated by the current sensor and detected by a receiving sensor; and
calculating a damage measurement for the sub-array from the collected data;
combining the damage measurement determined for each sub-array; and
determining an overall damage assessment from the combined damage measurements.

2. The method of claim 1 wherein the step of calculating a damage measurement further comprises:
comparing the damage measurement to a predetermined baseline measurement; and
determining a changed damage measurement from the difference between the damage measurement and the predetermined baseline measurement;
combining the changed damage measurement determined for each sub-array; and
determining an overall damage assessment from the combined changed damage measurements.

3. The method of claim 1, wherein each sub-array comprises the current sensor chosen from the plurality of sensors and neighboring sensors adjacent to the current sensor.

4. The method of claim 2 further comprising the step of discarding the damage measurement for each sub-array after the step of comparing the damage measurement to a predetermined baseline measurement.

5. The method of claim 1 wherein the step of decomposing the structural health monitoring system further comprises retrieving a pre-generated table comprising each sensor of the plurality of sensors associated with the neighbor sensors.

6. The method of claim 1 further comprising generating a damage report from the overall damage assessment.

7. A structural health monitoring system comprising:
a plurality of sensors mounted on a structure, the plurality of sensors decomposed into a plurality of sensor sub-arrays, each of the sub-arrays comprising one or more sensors that are also part of another sub-array of the plurality of sub-arrays;
a current sensor associated with each sub-array, each sensor in each sub-array configured to receive signals generated by the current sensor; and
a processor coupled to the plurality of sensors, the processor configured to calculate a sub-array damage assessment for each sub-array based on the signals received by the sensors, the processor further configured to calculate an overall damage assessment from each of the sub-array damage assessments.

8. The system of claim 7 wherein the processor is further configured to generate a sub-array change measurement by comparing the sub-array damage assessment to a baseline damage assessment and to combine the sub-array change measurements to form the overall damage assessment.

9. The system of claim 7 wherein the processor is further configured to generate a damage report from the overall damage assessment.

10. The system of claim 7 further comprising a memory coupled to the process, the memory storing a table comprising the plurality of sensors listed by a collection of overlapping sub-arrays.

11. The system of claim 7 further comprising one or more sensor data collected coupled between the sensors and the processor, the sensor data collectors configured to receive data from multiple sensors and to send the data to the processor over a single connection.

12. The system of claim 11 wherein the sensor data collectors are further configured to perform some processing of data collected by the sensors.

13. The system of claim 7 wherein the sensors are ultrasonic transducers.

14. The system of claim 13 wherein the ultrasonic transducers are operable to generate Lamb waves in the structure.

15. The system of claim 7 wherein the structure is the skin of an aircraft.

16. A method for the non-destructive testing of structures comprising:
decomposing an array of sensors into a series of overlapping sub-arrays of sensors;
performing a non-destructive test in each sub-array;
determining a sub-array damage assessment for each sub-array; and
combining all sub-array damage assessments to determine an overall damage assessment.

17. The method of claim 16 wherein the step of determining a sub-array damage assessment further comprises:
comparing each of the sub-array damage assessment to a predetermined baseline assessment;
determining a changed sub-array damage measurement from the difference between the sub-array damage assessment and the predetermined baseline assessment; and determining an overall damage assessment by combining the changed sub-array damage measurements determined for each sub-array.

18. The method of claim 16 wherein each sub-array comprises a current sensor chosen from the array of sensors and one or more neighbor sensors adjacent to the current sensor.

19. The method of claim 17 further comprising the step of discarding the sub-array damage assessment for each sub-array after the step of comparing each of the sub-array damage assessment to a predetermined baseline assessment.

20. The method of claim 17, wherein decomposing an array of sensors further comprises retrieving a pre-generated table comprising each sensor of the plurality of sensors associated with neighbor sensors in a set of sensor sub-arrays.

21. The method of claim 17 further comprising generating a damage report from the overall damage assessment.

* * * * *